(12) United States Patent
Hartung

(10) Patent No.: US 6,208,901 B1
(45) Date of Patent: *Mar. 27, 2001

(54) APPARATUS FOR DETERMINING THE AV TRANSMISSION TIME

(75) Inventor: Wolfgang Hartung, Magdeburg (DE)

(73) Assignee: Biotronik Mess-und Therapiegeraete GmbH & Co. Ingenieurbuero Berlin, Berlin (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/033,853

(22) Filed: Mar. 3, 1998

(30) Foreign Application Priority Data

Mar. 3, 1997 (DE) .............................. 197 11 058

(51) Int. Cl.[7] ...................................... A61N 1/365
(52) U.S. Cl. ................................. 607/23; 607/18
(58) Field of Search ................ 607/23, 24, 18, 607/119, 122

(56) References Cited

U.S. PATENT DOCUMENTS

| 4,600,017 | * | 7/1986 | Schroeppel | 607/122 |
| 5,334,222 | * | 8/1994 | Salo et al. | 607/24 |
| 5,417,717 | * | 5/1995 | Salo et al. | 607/24 |
| 5,626,623 | * | 5/1997 | Kieval et al. | 607/23 |

FOREIGN PATENT DOCUMENTS

| 494 487 A2 | 7/1992 | (AR) . |
| 450 387 A2 | 10/1991 | (DE) . |

OTHER PUBLICATIONS

Max Schaldach, Electrotherapy of the Heart—Technical Aspects in Cardiac Pacing, Springer Verlag Berlin, Heidelberg, 1992, pp. 58–60.

* cited by examiner

*Primary Examiner*—George R. Evanisko
(74) *Attorney, Agent, or Firm*—Venable; George H. Spencer; Robert Kinberg

(57) ABSTRACT

In an apparatus for determining the AV transmission time or AV delay in the heart, the apparatus having a signal-sensor arrangement that is disposed in the heart and detects a natural cardiac action, further having at least one signal output and a processing unit that has at least one signal input that is connected to the signal output of the signal-sensor arrangement for calculating the natural AV transmission time based on the detected cardiac action, the signal-receiver arrangement includes a pressure-sensor arrangement that is disposed in the vicinity of the tricuspid valve in the right atrium and/or in the right ventricle for detecting intracardial pressure changes associated with the opening of the tricuspid valve.

14 Claims, 3 Drawing Sheets

APPARATUS FOR DETERMINING THE AV TRANSMISSION TIME

FIELD OF THE INVENTION

The invention relates to an apparatus for monitoring heart performance and a pacemaker equipped with such an apparatus.

BACKGROUND OF THE INVENTION

Setting the time span between a natural or stimulated atrial action and the stimulation pulse for stimulating a ventricular action, the so-called AV delay, is of considerable significance for the hemodynamic optimization of pacemaker function and in connection with preventing pacemaker-induced tachycardia; see M. Schaldach, Electrotherapy of the Heart—Technical Aspects in Cardiac Pacing, Springer Verlag, Berlin, Heidelberg, 1992, pp. 58–60.

Hence, in recent years, pacemakers have been developed in which the AV delay, which was formerly fixed as a function of parameters that reflect the present state of a particular patient in a particular manner, can be changed. The reference basis is the current heart or stimulation rate, with the AV delay decreasing as the stimulation rate increases—see FIG. 30 on page 60 of the above-cited document.

EP 0 450 387 A2 describes an arrangement for automatic setting of the AV delay in a dual-chamber pacemaker, taking into consideration (patient-specific) intra-atrial delay times.

EP 0 494 487 A2 describes an AV-sequential, dual-chamber pacemaker having automatic AV delay programming, in which an objective is to consider pacemaker-stipulated, interatrial and interventricular transmission times. In a test phase prior to the actual pacing, the natural heart rate and a natural AV delay—as a temporal difference between either the natural P wave or an atrial pacemaker "spike" and the natural R wave or a ventricular pacemaker "spike" (with all signals being detected via the pacemaker electrodes)—are determined.

Because this arrangement cannot provide normal stimulation during the test phase, a value of the AV delay obtained from several (for example, four) natural cardiac actions constitutes the basis of a subsequent, long-term stimulation phase (for example, 100 pulses). A truly near-time determination and use of a current AV delay for controlling the pacemaker is therefore not possible, so the pacemaker cannot operate hemodynamically optimally with respect to sudden changes in state, such as the onset or cessation of stresses in the patient.

This disadvantage, of course, also affects the known methods of determining the AV transmission time from a surface EKG, echo-cardiographic methods and the like, because these tests cannot be performed on the patient on a daily, permanent basis.

OBJECTS AND SUMMARY OF THE INVENTION

It is an object of the invention to provide an apparatus for monitoring heart performance, specifically AV transmission time, and which—particularly in connection with a cardiac pacemaker—is suited for permanent use in the patient. It is an additional object of the invention to provide a pacemaker equipped with such an apparatus.

The invention includes the concept of performing a near-time or real-time determination of the natural AV transmission time on a mechanical basis, utilizing the correlation between characteristic stimulation states of the conductive heart tissue and the respective mechanical state of the heart. The invention utilizes the knowledge that characteristic signals in the surface EKG or corresponding changes in the bundle of His potential that are detected in the recording of an intracardial EKG, and which can be used to determine the AV transmission time, have a mechanical equivalent in the valve movements of the tricuspid valve, in particular, or intracardial pressure fluctuations. It could be determined, in particular, that pressure spikes occur synchronously with the R wave and at the beginning of the P wave.

To suppress interference, an embodiment can advantageously encompass a pressure- or movement-sensor arrangement comprising a plurality of pressure or movement sensors that are disposed in different positions relative to the tricuspid valve, with each sensor having a signal output; and a processing unit having a number of individual signal inputs corresponding to the number of pressure or movement sensors, as well as means for common evaluation of the signals received by the sensors, taking into consideration the respective signal time delay.

With this type of arrangement, a plurality of essentially identical pressure or movement signals can be obtained, the signals being offset in time with respect to one another due to the limited speed of the intracardial pressure propagation. The signals can be used to increase the signal/noise ratio by means of, for example, signal accumulation (following elimination of the time offset) or correlation analysis.

In a useful embodiment, at least one pressure or movement sensor is disposed in the atrium, and at least one is disposed in the ventricle.

An embodiment that serves as an alternative, or supplement, to the aforementioned variation, and has increased suppression of interference, is characterized in that sensor means, which are provided with a signal output for detecting a spontaneous or induced atrial signal, are associated with the processing unit, the signal output being connected to a corresponding signal input of the processing unit. Furthermore, the processing unit includes timing means and switching means for blocking the signal input connected to the pressure- or movement-sensor arrangement in order to preset a time window for detecting the input signals of the pressure- or movement-sensor arrangement. This time window is opened upon the perception of an atrial signal or stimulation, and only remains open for the time span during which the systolic pressure increase is a factor, that is, about 250–300 ms. Pressure fluctuations occurring outside of this time frame, which can only represent interference signals for the provided measurement anyway, are excluded at the outset from any processing.

In an embodiment that is particularly flexible with respect to evaluation options, the processing unit includes means for discriminating movement and pressure components in a signal of a pressure or movement sensor, for example, at least one low-frequency bandpass filter. The design and/or programming of the actual evaluation stages is or are tailored to the respective, specific information content of the course of valve movement or the intracardial changes in pressure that are resolved by movement influences.

The sensor arrangement is advantageously disposed on a cardiac catheter. One of skill in the art can embody the arrangement corresponding to known sensors for intraarterial or intracardial blood-pressure measurement. In an advantageous embodiment, the arrangement has, for example, a sensor, particularly a piezoelectric pressure sensor, that detects the movement or deformation of a pressure-sensor surface on the electrical path, or a sensor that detects this movement or deformation on the optical path, particularly through the diversion or changing of the transmission of a light bundle that is directed at the surface and transmitted via fiber optics to the measurement site. In an arrangement having a plurality of pressure sensors, a plurality of pressure-sensing surfaces that are formed or connected by jacket-surface segments of the cardiac catheter that are separated by one another are disposed on the cardiac catheter.

To ensure a detection of pressure or movement without the influence of wall contacts, the cardiac catheter is constructed with a bending resistance and, possibly, is provided with a preset curvature over its length such that it can be positioned, exposed, in the atrium and/or the ventricle essentially without contact between the pressure-sensor surfaces and the inside walls of the heart.

To determine the AV delay with respect to a detected, natural atrial signal, at least one electrode should be provided in the atrium for receiving a cardiac-action potential. The electrode is connected to a corresponding signal input of the processing unit, and the processing unit includes means for determining the time interval between a signal that has been derived from the cardiac-action potential and a signal that has been supplied by the pressure- or movement-sensor arrangement. Such means are well-known as suitable electrode superstructures of conventional pacemakers. With the use of two or more electrodes, differential detection of the atrial signal is advantageously possible.

To determine the AV delay with respect to an artificial stimulation pulse, an apparatus for generating the stimulation pulse and transmitting it to the atrium should be provided, the apparatus having a signal output that is connected to a corresponding signal input of the processing unit, and the processing unit including means for determining the time interval between an emitted stimulation pulse and a signal supplied by the pressure- or movement-sensor arrangement. The apparatus for generating the stimulation pulse can, of course, be the corresponding part of a conventional pacemaker, and a present atrial electrode may be used for transmission.

BRIEF DESCRIPTION OF THE DRAWINGS

Advantageous modifications of the invention are characterized in the dependent claims and described below in the description of the preferred embodiment of the invention, in conjunction with the figures, in which

DETAILED DESCRIPTION OF THE PREFERRED EMBODIMENT

Figure 1:
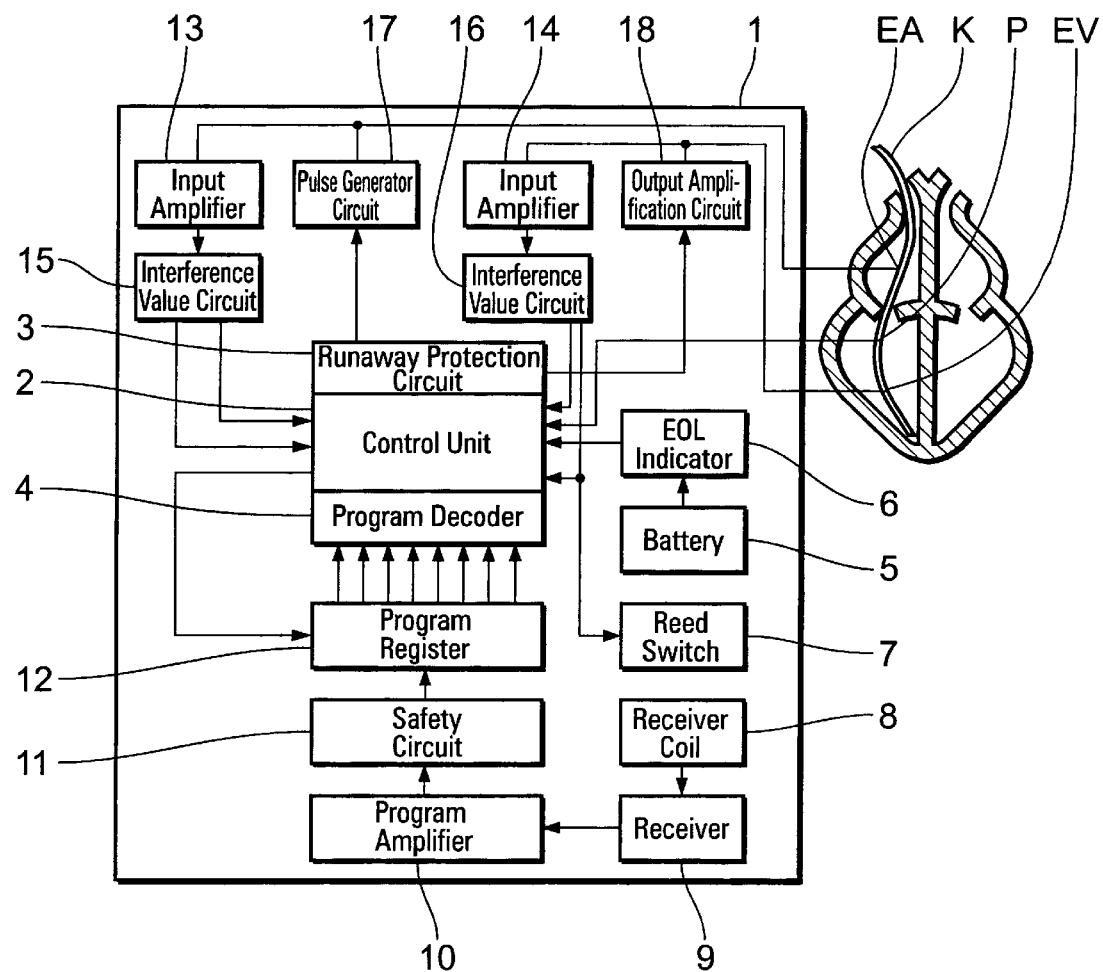
FIG. 1 is a block diagram of an externally-programmable AV-sequential, dual-chamber pacemaker with an associated cardiac catheter, with which an embodiment of the invention is realized.

The design of the dual-chamber pacemaker 1 illustrated in FIG. 1 is essentially known per se, and will only be outlined briefly: The core component is a control unit 2, with which a circuit 3 for "runaway" protection and a program decoder 4 are directly associated. A battery 5 having a downstream EOL indicator 6 supplies the pacemaker with energy. Upon activation by a reed switch 7, a program register 12 is charged by way of a receiver coil 8, a receiver 9, a program amplifier 10 and a safety circuit 11 for program checking; program data can be queried from this register by the control unit.

A cardiac catheter K, which has a (right) atrial and a (right) ventricular electrode arrangement EA and EV, respectively, and a pressure-sensor arrangement P, is associated with the pacemaker 1. Cardiac action potentials are detected by way of the electrode arrangements EA and EV, and are supplied to the control unit 2 by way of an input amplifier 13 for atrial signals and an input amplifier 14 for ventricular signals, with downstream interference-value circuits 15 and 16, respectively. Signals from the pressure-sensor arrangement P, which reflect intracardial pressure changes due to movements of the heart valves, are likewise supplied to the control unit. The aforementioned input signals are subjected to processing in the control unit 2, and are used to control the pacemaker corresponding to the patient's present cardiac output needs.

Stimulation pulses are generated with corresponding parameters in a pulse-generator circuit and an output-amplification circuit 17 and 18, respectively, and supplied to the electrode arrangements EA or EV, and finally transmitted from them to the heart tissue to be stimulated.

Figure 2:
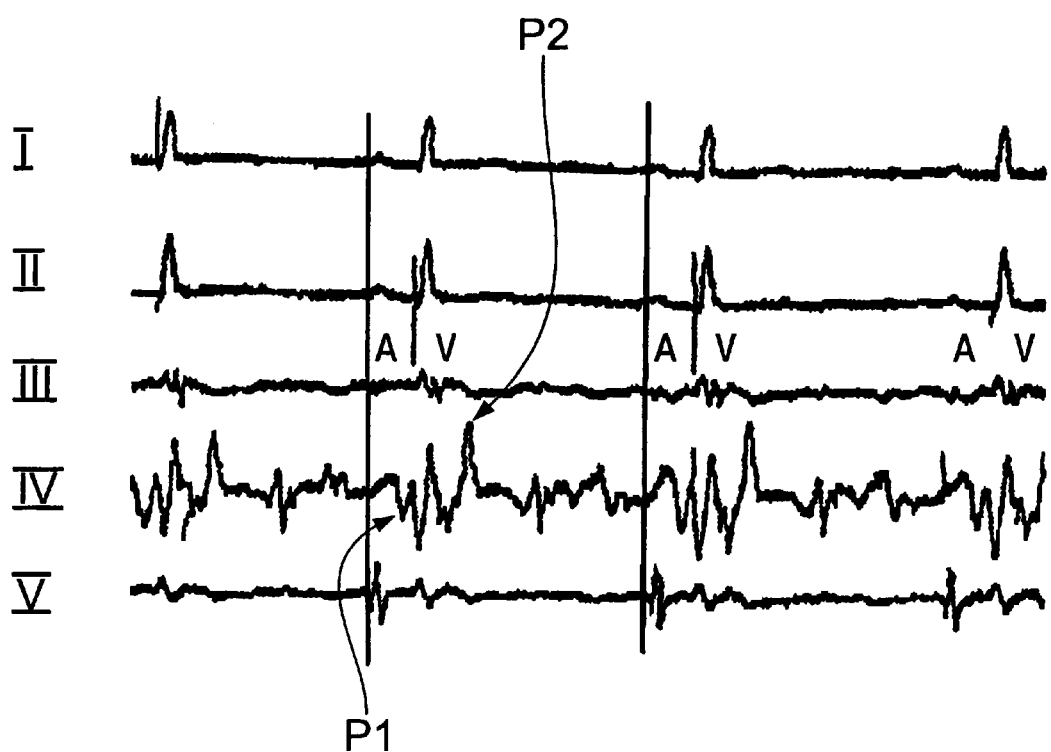
FIG. 2 is a comparative illustration of the signal courses in different measuring methods for detecting cardiac actions.

FIG. 2 is a comparative representation of the signal courses in different measurement methods for detecting cardiac actions; this illustration should be considered in connection with the determination of the AV transmission time or delay.

The signal courses I and II are surface-EKG diagrams, and curve III shows a bundle of His electrogram, i.e., the result of an intracardial registration of the cardiac-action potentials. "A" and "V" respectively indicate an atrial or ventricular stimulation pulse.

Curve IV shows registrations by means of an intracardially (especially right-atrially) positioned pressure sensor referred to as a "piezo cath." It can be seen that detectable pressure fluctuations occur in synchronization with the cardiac actions, with the course of the curve illustrating characteristic points—for example, the points indicated by "P1" and "P2". P1 is associated with the beginning of the opening of the tricuspid valve, and P2 is associated with the end of systole.

The two points P1 and P2 can be used as trigger points for determining the AV transmission time or delay, instead of the R peak of the EKG or a corresponding registration in the bundle of His electrogram (HBE), whereby the pressure measurement can replace an electrographic measurement for determining the AV delay—particularly in a real-time determination for adapting a corresponding pacemaker setting to the current hemodynamic needs of the patient.

Assuming P2 as a trigger point (TgP), an approximate real-time AV determination can be performed with, for example, the relationship $$AV\text{delay}_n = aST_n + (aST_{n-1} \cdot TgP_{n-1} - x \text{ ms})$$

where $aST_n$ = n-th atrial stimulation/n-th sensing, $aST_{n-1}$ = (n−1)th atrial stimulation/(n−1)th sensing, $TgP_{n-1}$ = trigger point in the (n−1)th atrial stimulation/the (n−1)th sensing, x ms=time span by which the optimum stimulation of the ventricle precedes the trigger point, (x=desired value).

A temporal and local differentiation of interference signals is possible through the detection and corresponding evaluation of signals of a plurality of pressure sensors disposed with varying spacing from the tricuspid valve—particularly, one behind the other on a catheter. For this purpose, signal processing can be supplemented by signal-accumulation and/or signal-correlation methods.

A further option for suppressing interference is the operation of the pressure sensor or sensors in a time window (for example, 250 to 300 ms) that begins with the atrial signal detection or stimulation.

Figure 3B:
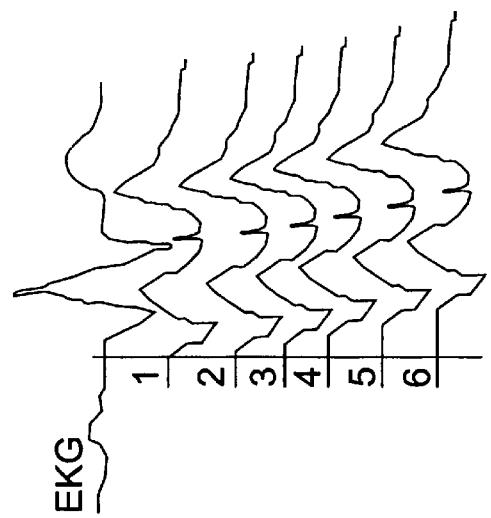
FIG. 3b shows illustrations of temporal signal courses of the pressure sensors shown in FIG. 3a, in comparison to the signal course of a surface EKG recorded in parallel.
Figure 3A:
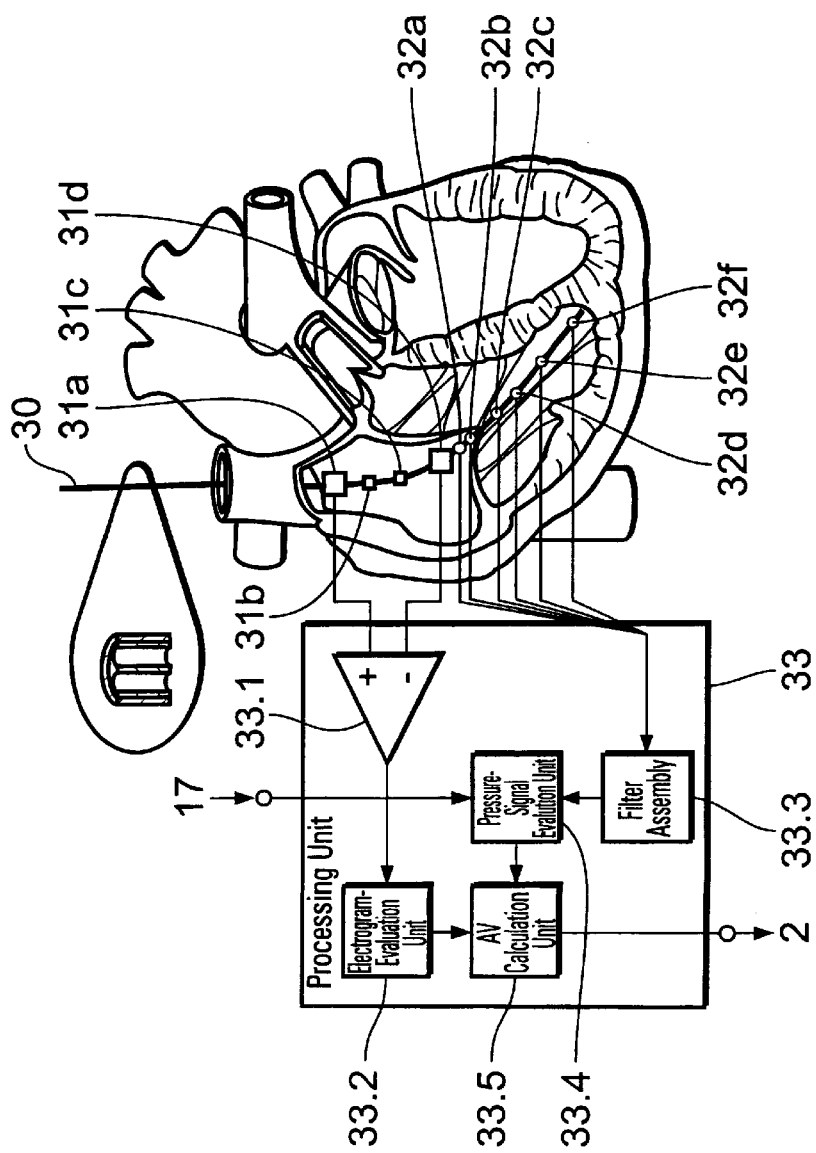
FIG. 3a is a schematic general view of a cardiac catheter that is used in the embodiment of the invention with electrode segments for detecting an intracardial EKG and a plurality of pressure sensors when the catheter is inserted into the heart.

FIG. 3a shows a very schematic general view of a cardiac catheter 30 that is inserted into a heart, the catheter having electrode segments 31a through 31d for detecting an intracardial EKG or the starting point for the natural AV transmission time, and six identical pressure sensors 32a through 32f for detecting one of the aforementioned trigger points. FIG. 3b shows representations of temporal signal courses of the pressure sensors shown in FIG. 3a, in comparison to the signal course of a surface EKG recorded in parallel (by means of an EKG arrangement, not shown).

The pressure sensors 32a through 32f are disposed in a row that extends from the region of the atrium near the valve into the apex of the heart, that is, it extends with varying spacing from the tricuspid valve.

Stimulation pulses can be applied by way of the electrodes 31a through 31d, and cardiac actions can be detected in the atrium in a differential, bipolar manner. A difference amplifier 33.1 that is connected to the electrodes 31a and 31d, and an electrogram-evaluation unit 33.2 connected to its output, are shown in the figure as parts of a processing unit 33 that are provided for this purpose. A good separation between the antegrade and the retrograde atrial signals is possible with suitable input filters. A suitable embodiment of the signal detection can practically preclude an erroneous sensing, as well as pacemaker-induced tachycardia.

With increasing distance from the tricuspid valve, the pressure sensors 32a through 32f supply temporally-offset signals having a very similar signal shape, as can be seen in lines 1 through 6 (corresponding to the pressure sensors 32a through 32f) in FIG. 3b. This offers the option of the above-described evaluation in a pressure-signal evaluation unit 33.4 that is triggered by the atrial pulse generator 17 (FIG. 1) following separation of movement components in a filter assembly 33.3.

The outputs of the pressure-signal evaluation unit 33.4 and the electrogram-evaluation unit 33.2 are connected to an AV calculation unit 33.5 for calculating the AV delay; the output of the calculation unit is connected to the control unit 2 of the pacemaker (FIG. 1).

As can be seen from FIG. 3a, in the atrium, the cardiac catheter 30 advantageously receives all lines for determining the AV delay and stimulation in a single branch configured as a double line (as shown in the oval window). With the suitably rigid embodiment of the conductors and/or insulation, and possibly the provision of an additional, predetermined curvature, the catheter is configured mechanically so as to have no contact with the walls of the heart.

In an advantageous embodiment, the pressure sensors 32a through 32f have elastically-deformable pressure surfaces or membrane segments at the catheter surface, with a sensor being associated with one of these deformable segments, so the above-described sensor types can be used here.

The invention is not limited to the above-described, preferred embodiment. Rather, numerous variations are conceivable that make use of the illustrated solution, even in different embodiments.

What is claimed is:

1. An apparatus for determining a natural AV transmission time or a natural AV delay in a heart, comprising:
   a signal-sensor arrangement for being disposed in the heart and to detect a natural cardiac action, said signal-sensor arrangement having at least one signal output and having a pressure- or movement-sensor arrangement for being disposed near the tricuspid valve in at least one of the right atrium and the right ventricle, said pressure- or movement-sensor arrangement detecting movements of the tricuspid valve, wherein the pressure-sensor arrangement includes a plurality of pressure sensors for being disposed at different positions relative to the tricuspid valve, each having a signal output;
   at least one electrode for being provided in the heart for sensing a cardiac-action potential, said at least one electrode having at least one signal output; and
   a processing unit having a plurality of signal inputs, the plurality of signal inputs including a number of signal inputs corresponding to the number of the plurality of pressure sensors, at least one of said signal inputs being connected to the at least one signal output of the signal-sensor arrangement and at least one of said signal inputs being connected to the at least one signal output of said at least one electrode, the processing unit calculating at least one of the natural AV transmission time and the natural AV delay based on cardiac action detected using the signal-sensor arrangement and on said cardiac-action potential detected using said at least one electrode, said processing unit including:
      means for determining a time interval between a signal sensed by the electrode and representing said cardiac-action potential and a signal supplied by the at least one of a pressure-sensor arrangement and a movement-sensor arrangement, said time interval being used for the computation of the natural AV transmission time or the natural AV delay; and
      means for evaluating signals received from the signal outputs of the plurality of pressure sensors at said signal inputs, said means for evaluating taking into consideration respective time delays of the signals.

2. The apparatus according to claim 1, wherein at least one of said plurality of pressure sensors is for being disposed in the atrium and at least one is for being disposed in the ventricle.

3. An apparatus for determining a natural AV transmission time or a natural AV delay in a heart, comprising:
   a signal-sensor arrangement for being disposed in the heart and to detect a natural cardiac action, said signal-sensor arrangement having at least one signal output and having a pressure- or movement-sensor arrangement for being disposed near the tricuspid valve in at least one of the right atrium and the right ventricle, said pressure- or movement-sensor arrangement detecting movements of the tricuspid valve;
   at least one electrode for being provided in the heart for sensing a cardiac-action potential, said at least one electrode having at least one signal output;
   a processing unit having at least two signal inputs, at least one of said signal inputs being connected to the at least one signal output of the signal-sensor arrangement and at least one of said signal inputs being connected to the at least one signal output of said at least one electrode, the processing unit calculating at least one of the natural AV transmission time and the natural AV delay based on cardiac action detected using the signal-sensor arrangement and on said cardiac-action potential detected using said at least one electrode, said processing unit including:

means for determining a time interval between a signal sensed by the electrode and representing said cardiac-action potential and a signal supplied by the at least one of a pressure-sensor arrangement and a movement-sensor arrangement, said time interval being used for the computation of the natural AV transmission time or the natural AV delay; and timing means and switching means, which timing means and switching means serve to effect blocking of the at least one signal input that is connected to the at least one signal output of the signal-sensor arrangement, for presetting a time window for detecting signals generated by the signal-sensor arrangement; and sensing means having a signal output connected to the processing unit for detecting a spontaneous or induced atrial signal, the signal output being connected to a corresponding signal input of the processing unit.

4. An apparatus for determining a natural AV transmission time or a natural AV delay in a heart, comprising:

a signal-sensor arrangement for being disposed in the heart and to detect a natural cardiac action, said signal-sensor arrangement having at least one signal output and having a pressure- or movement-sensor arrangement for being disposed near the tricuspid valve in at least one of the right atrium and the right ventricle, said pressure- or movement-sensor arrangement detecting movements of the tricuspid valve, the signal-sensor arrangement further including:

a sensor that detects movement or deformity of a pressure-sensor surface on an electrical path;

a cardiac catheter; and a plurality of pressure-sensor surfaces disposed on the cardiac catheter, the catheter having jacket-surface segments that are separated from one another, said pressure-sensor surfaces being formed on or connected to the catheter by said jacket-surface segments;

at least one electrode for being provided in the heart for sensing a cardiac-action potential, said at least one electrode having at least one signal output; and a processing unit having at least two signal inputs, at least one of said signal inputs being connected to the at least one signal output of the signal-sensor arrangement and at least one of said signal inputs being connected to the at least one signal output of said at least one electrode, the processing unit calculating at least one of the natural AV transmission time and the natural AV delay based on cardiac action detected using the signal-sensor arrangement and on said cardiac-action potential detected using said at least one electrode, said processing unit including:

means for determining a time interval between a signal sensed by the electrode and representing said cardiac-action potential and a signal supplied by the at least one of a pressure-sensor arrangement and a movement-sensor arrangement, said time interval being used for the computation of the natural AV transmission time or the natural AV delay.

5. An apparatus for determining a natural AV transmission time or a natural AV delay in a heart, comprising:

a signal-sensor arrangement for being disposed in the heart and to detect a natural cardiac action, said signal-sensor arrangement having at least one signal output and having a pressure- or movement-sensor arrangement for being disposed near the tricuspid valve in at least one of the right atrium and the right ventricle, said pressure- or movement-sensor arrangement detecting movements of the tricuspid valve wherein the movement-sensor arrangement includes a plurality of movement sensors that are disposed at different positions relative to the tricuspid valve, each having a signal output;

at least one electrode for being provided in the heart for sensing a cardiac-action potential, said at least one electrode having at least one signal output; and a processing unit having a plurality of signal inputs, the plurality of signal inputs including a number of signal inputs corresponding to the number of the plurality of movement sensors, at least one of said signal inputs being connected to at least one of the signal outputs of the signal-sensor arrangement, and at least one of said signal inputs being connected to the at least one signal output of said at least one electrode, the processing unit calculating at least one of the natural AV transmission time and the natural AV delay based on cardiac action detected using the signal-sensor arrangement and on said cardiac-action potential detected using said at least one electrode, said processing unit including:

means for determining a time interval between a signal sensed by the electrode and representing said cardiac-action potential and a signal supplied by the at least one of a pressure-sensor arrangement and a movement-sensor arrangement, said time interval being used for the computation of the natural AV transmission time or the natural AV delay; and means for evaluating signals received from the signal outputs of the plurality of movement sensors at the signal inputs, said means for evaluating taking into consideration any relative time delays of the signals.

6. The apparatus according to claim 5, wherein at least one of said plurality of movement sensors is for being disposed in the atrium and at least one is for being disposed in the ventricle.

7. An apparatus for determining a natural AV transmission time or a natural AV delay in a heart, comprising:

a signal-sensor arrangement for being disposed in the heart and to detect a natural cardiac action, said signal-sensor arrangement having at least one signal output and having a pressure- or movement-sensor arrangement for being disposed near the tricuspid valve in at least one of the right atrium and the right ventricle, said pressure- or movement-sensor arrangement detecting movements of the tricuspid valve;

at least one electrode for being provided in the heart for sensing a cardiac-action potential, said at least one electrode having at least one signal output; and a processing unit having at least two signal inputs, at least one of said signal inputs being connected to the at least one signal output of the signal-sensor arrangement and at least one of said signal inputs being connected to the at least one signal output of said at least one electrode, the processing unit calculating at least one of the natural AV transmission time and the natural AV delay based on cardiac action detected using the signal-sensor arrangement and on said cardiac-action potential detected using said at least one electrode, said processing unit including:
  means for determining a time interval between a signal sensed by the electrode and representing said cardiac-action potential and a signal supplied by the at least one of a pressure-sensor arrangement and a movement-sensor arrangement, said time interval being used for the computation of the natural AV transmission time or the natural AV delay; and
  means for discriminating movement and pressure components in the signals of the pressure- or movement-sensor arrangement, including at least one low-frequency bandpass filter.

8. An apparatus for determining a natural AV transmission time or a natural AV delay in a heart, comprising:
  a signal-sensor arrangement for being disposed in the heart and to detect a natural cardiac action, said signal-sensor arrangement having at least one signal output and having a pressure- or movement-sensor arrangement for being disposed near the tricuspid valve in at least one of the right atrium and the right ventricle, said pressure- or movement sensor arrangement detecting movements of the tricuspid valve, the pressure-sensor arrangement including a plurality of pressure sensors for being disposed at different positions relative to the tricuspid valve, each having a signal output;
  a device for generating a stimulation pulse and transmitting the stimulation pulse to the atrium of the heart, the device having a signal output; and
  a processing unit having a plurality of signal inputs, the plurality of signal inputs including a number of signal inputs corresponding to the number of the plurality of pressure sensors, at least one of said signal inputs being connected to at least one of the signal outputs of the signal-sensor arrangement, and at least one of said signal inputs being connected to the signal output of said device for generating a stimulation pulse, the processing unit the natural AV transmission time or the natural AV delay based on cardiac action detected using the signal-sensor arrangement and on a stimulation pulse generated by said device for generating a stimulation pulse, said processing unit including:
    means for determining a time interval between a stimulation pulse generated by said device for generating a stimulation pulse and a signal supplied by the at least one of a pressure-sensor arrangement and a movement-sensor arrangement, said time interval being used for the computation of the natural AV transmission time or the natural AV delay; and
    means for evaluating signals received from the signal outputs of the plurality of pressure sensors at said signal inputs, said means for evaluating taking into consideration respective time delays of the signals.

9. The apparatus according to claim 8, wherein at least one of said plurality of pressure sensors is for being disposed in the atrium and at least one is for being disposed in the ventricle.

10. An apparatus for determining a natural AV transmission time or a natural AV delay in a heart, comprising:
  a signal-sensor arrangement for being disposed in the heart and to detect a natural cardiac action, said signal-sensor arrangement having at least one signal output and having a pressure- or movement-sensor arrangement for being disposed near the tricuspid valve in at least one of the right atrium and the right ventricle, said pressure- or movement sensor arrangement detecting movements of the tricuspid valve;
  a device for generating a stimulation pulse and transmitting the stimulation pulse to the atrium of the heart, the device having a signal output;
  a processing unit having at least two signal inputs, at least one of said signal inputs being connected to the at least one signal output of the signal-sensor arrangement and at least one of said signal inputs being connected to the signal output of said device for generating a stimulation pulse, the processing unit the natural AV transmission time or the natural AV delay based on cardiac action detected using the signal-sensor arrangement and on a stimulation pulse generated by said device for generating a stimulation pulse, said processing unit including:
    means for determining a time interval between a stimulation pulse generated by said device for generating a stimulation pulse and a signal supplied by the at least one of a pressure-sensor arrangement and a movement-sensor arrangement, said time interval being used for the computation of the natural AV transmission time or the natural AV delay; and
    timing means and switching means, which timing means and switching means serve to effect blocking of the at least one signal input that is connected to the at least one signal output of the signal-sensor arrangement, for presetting a time window for detecting signals generated by the signal-sensor arrangement; and
  sensing means having a signal output connected to the processing unit for detecting a spontaneous or induced atrial signal, the signal output being connected to a corresponding signal input of the processing unit.

11. An apparatus for determining a natural AV transmission time or a natural AV delay in a heart, comprising:
  a signal-sensor arrangement for being disposed in the heart and to detect a natural cardiac action, said signal-sensor arrangement having at least one signal output and having a pressure- or movement-sensor arrangement for being disposed near the tricuspid valve in at least one of the right atrium and the right ventricle, said pressure- or movement sensor arrangement detecting movements of the tricuspid valve;
  a device for generating a stimulation pulse and transmitting the stimulation pulse to the atrium of the heart, the device having a signal output; and
  a processing unit having at least two signal inputs, at least one of said signal inputs being connected to the at least one signal output of the signal-sensor arrangement and at least one of said signal inputs being connected to the signal output of said device for generating a stimulation pulse, the processing unit the natural AV transmission time or the natural AV delay based on cardiac action detected using the signal-sensor arrangement and on a stimulation pulse generated by said device for generating a stimulation pulse, said processing unit including:
    means for determining a time interval between a stimulation pulse generated by said device for generating a stimulation pulse and a signal supplied by the at least one of a pressure-sensor arrangement and a movement-sensor arrangement, said time interval being used for the computation of the natural AV transmission time or the natural AV delay; and
    means for discriminating movement and pressure components in the signals of the pressure- or movement-sensor arrangement, including at least one low-frequency bandpass filter.

12. An apparatus for determining a natural AV transmission time or a natural AV delay in a heart, comprising:
- a signal-sensor arrangement for being disposed in the heart and to detect a natural cardiac action, said signal-sensor arrangement having at least one signal output and having a pressure- or movement-sensor arrangement for being disposed near the tricuspid valve in at least one of the right atrium and the right ventricle, said pressure- or movement sensor arrangement detecting movements of the tricuspid valve, the signal-sensor arrangement further comprising:
  - a sensor that detects movement or deformity of a pressure-sensor surface on an electrical path;
  - a cardiac catheter; and
  - a plurality of pressure-sensor surfaces disposed on the cardiac catheter, the catheter having jacket-surface segments that are separated from one another, said pressure-sensor surfaces being formed on or connected to the catheter by said jacket-surface segments;
- a device for generating a stimulation pulse and transmitting the stimulation pulse to the atrium of the heart, the device having a signal output; and
- a processing unit having at least two signal inputs, at least one of said signal inputs being connected to the at least one signal output of the signal-sensor arrangement and at least one of said signal inputs being connected to the signal output of said device for generating a stimulation pulse, the processing unit the natural AV transmission time or the natural AV delay based on cardiac action detected using the signal-sensor arrangement and on a stimulation pulse generated by said device for generating a stimulation pulse, said processing unit including:
  - means for determining a time interval between a stimulation pulse generated by said device for generating a stimulation pulse and a signal supplied by the at least one of a pressure-sensor arrangement and a movement-sensor arrangement, said time interval being used for the computation of the natural AV transmission time or the natural AV delay.

13. An apparatus for determining a natural AV transmission time or a natural AV delay in a heart, comprising:
- a signal-sensor arrangement for being disposed in the heart and to detect a natural cardiac action, said signal-sensor arrangement having at least one signal output and having a pressure- or movement-sensor arrangement for being disposed near the tricuspid valve in at least one of the right atrium and the right ventricle, said pressure- or movement sensor arrangement detecting movements of the tricuspid valve, the movement-sensor arrangement including a plurality of movement sensors that are disposed at different positions relative to the tricuspid valve, each having a signal output;
- a device for generating a stimulation pulse and transmitting the stimulation pulse to the atrium of the heart, the device having a signal output; and
- a processing unit having a plurality of signal inputs, the plurality of signal inputs including a number of signal inputs corresponding to the number of said plurality of movement sensors, at least one of said signal inputs being connected to the at least one signal output of the signal-sensor arrangement and at least one of said signal inputs being connected to the signal output of said device for generating a stimulation pulse, the processing unit the natural AV transmission time or the natural AV delay based on cardiac action detected using the signal-sensor arrangement and on a stimulation pulse generated by said device for generating a stimulation pulse, said processing unit including:
  - means for determining a time interval between a stimulation pulse generated by said device for generating a stimulation pulse and a signal supplied by the at least one of a pressure-sensor arrangement and a movement-sensor arrangement, said time interval being used for the computation of the natural AV transmission time or the natural AV delay; and
  - means for evaluating signals received from the signal outputs of the plurality of movement sensors at the signal inputs, said means for evaluating taking into consideration any relative time delays of the signals.

14. The apparatus according to claim 13, wherein at least one of said plurality of movement sensors is for being disposed in the atrium and at least one is for being disposed in the ventricle.

* * * * *